(12) United States Patent
Amrich

(10) Patent No.: US 6,620,332 B2
(45) Date of Patent: Sep. 16, 2003

(54) METHOD FOR MAKING A MESH-AND-PLATE SURGICAL IMPLANT

(75) Inventor: Mark P. Amrich, Tyngsborough, MA (US)

(73) Assignee: Tecomet, Inc., Wilmington, MA (US)

( * ) Notice: Subject to any disclaimer, the term of this patent is extended or adjusted under 35 U.S.C. 154(b) by 0 days.

(21) Appl. No.: 10/021,616

(22) Filed: Dec. 12, 2001

(65) Prior Publication Data

US 2002/0173854 A1 Nov. 21, 2002

Related U.S. Application Data

(60) Provisional application No. 60/309,923, filed on Aug. 3, 2001, provisional application No. 60/291,002, filed on May 15, 2001, and provisional application No. 60/264,084, filed on Jan. 25, 2001.

(51) Int. Cl.[7] .................................................. C23F 1/00
(52) U.S. Cl. ........................... 216/11; 216/47; 216/52; 216/56; 216/100; 216/109
(58) Field of Search ............................... 216/11, 47, 49, 216/52, 56, 100, 108, 109; 623/11.11, 23.53–23.55, 23.76, 9.9, 923

(56) References Cited

U.S. PATENT DOCUMENTS

| 852,873 | A | 5/1907 | Davidson | |
|---|---|---|---|---|
| 3,046,321 | A | 7/1962 | McDermott | |
| 3,359,192 | A | 12/1967 | Heinrich et al. | 204/143 |
| 3,605,123 | A | 9/1971 | Hahn | |
| 3,679,500 | A | 7/1972 | Kubo et al. | 156/11 |
| 3,905,080 | A | 9/1975 | Bond | |
| 4,033,831 | A | 7/1977 | Bakewell | 204/11 |
| 4,069,085 | A | 1/1978 | Buysman et al. | 156/345 |
| 4,272,855 | A | 6/1981 | Frey | |
| 4,284,468 | A | 8/1981 | Stearns | 156/661.1 |
| 4,330,891 | A | 5/1982 | Branemark et al. | |
| 4,355,428 | A | 10/1982 | Deloison et al. | |
| 4,422,465 | A | 12/1983 | Haga | |
| 4,456,500 | A | 6/1984 | Ibata | |
| 4,470,872 | A | 9/1984 | Sudo et al. | |
| 4,528,070 | A | 7/1985 | Gamblin | 204/11 |
| 4,608,052 | A | 8/1986 | Van Kampen et al. | |
| 4,632,726 | A | 12/1986 | Thoms | 156/644 |

(List continued on next page.)

FOREIGN PATENT DOCUMENTS

| GB | 2206614 | 1/1989 |
|---|---|---|
| JP | 06125978 | 5/1994 |

OTHER PUBLICATIONS

International Search Report, Application Serial No. PCT/US02/13618, Oct. 3, 2002.
International Serch Report, Application Serial No. PCT/US02/02066, Oct. 3, 2002.

*Primary Examiner*—Anita Alanko
(74) *Attorney, Agent, or Firm*—Morgan, Lewis & Bockius, LLP

(57) ABSTRACT

Method for making a mesh-and-plate surgical implant includes the steps of applying maskant to first and second faces of a metal sheet, selectively ablating the maskant on both faces, affixing a first tape to the first face to cover same and maskant thereon, but leaving an exposed portion for a screw hole, affixing a second tape to the second face to cover same and maskant thereon, etching the first face screw hole portion to form a crater, removing the first tape, etching the crater and other exposed portions of the first face, removing the second tape, etching opposite the crater and other exposed portions of the second face to provide openings in communication with the crater, and other second face openings extending to the first face, and removing remaining maskant to provide the implant configured to include a pliable mesh portion and a rigid plate portion, and having a screw hole therein.

10 Claims, 5 Drawing Sheets

U.S. PATENT DOCUMENTS

| | | | | |
|---|---|---|---|---|
| 4,634,603 | A | 1/1987 | Gruss et al. | |
| 4,644,942 | A | 2/1987 | Sump | |
| 4,662,984 | A | 5/1987 | Ohtake et al. | 156/637 |
| 4,664,668 | A | 5/1987 | Beck et al. | |
| 4,673,409 | A | 6/1987 | Van Kampen | |
| 4,714,470 | A | 12/1987 | Webb, Jr. et al. | |
| 4,725,334 | A | 2/1988 | Brimm | 156/630 |
| 4,752,294 | A | 6/1988 | Lundgren | |
| 4,803,098 | A | 2/1989 | Henri et al. | |
| 4,834,756 | A | 5/1989 | Kenna | |
| 4,836,837 | A | 6/1989 | Rapp | |
| 4,836,884 | A | 6/1989 | McAuslan | |
| 4,846,839 | A | 7/1989 | Noiles | |
| 4,851,008 | A | 7/1989 | Johnson | |
| 4,863,474 | A | 9/1989 | Brown et al. | |
| 4,863,475 | A | 9/1989 | Andersen et al. | |
| 4,865,603 | A | 9/1989 | Noiles | 623/18 |
| 4,871,366 | A | 10/1989 | von Recum et al. | |
| 4,900,387 | A | 2/1990 | Johnson | |
| 4,900,398 | A | 2/1990 | Chen | 156/664 |
| H788 | H | 6/1990 | Schneider, Jr. | |
| 4,944,763 | A | 7/1990 | Willert et al. | 623/23 |
| 4,955,909 | A | 9/1990 | Ersek et al. | |
| 4,959,275 | A | 9/1990 | Iguchi et al. | |
| 4,960,381 | A | 10/1990 | Niznick | |
| 4,969,904 | A | 11/1990 | Koch et al | |
| 4,976,738 | A | 12/1990 | Frey et al. | |
| 4,978,358 | A | 12/1990 | Bobyn | |
| 4,989,304 | A | 2/1991 | Sonefors | |
| 5,002,572 | A | 3/1991 | Picha | |
| 5,002,575 | A | 3/1991 | Johnson | |
| 5,002,580 | A | 3/1991 | Noble et al. | |
| 5,007,931 | A | 4/1991 | Smith | |
| 5,011,494 | A | 4/1991 | von Recum et al. | |
| 5,100,508 | A | 3/1992 | Yoshida et al. | |
| 5,108,434 | A | 4/1992 | Ahrens et al. | |
| 5,139,528 | A | 8/1992 | Koch et al. | |
| 5,207,709 | A | 5/1993 | Picha | |
| 5,219,361 | A | 6/1993 | von Recum et al. | |
| 5,222,983 | A | 6/1993 | Schmitz et al. | |
| 5,236,459 | A | 8/1993 | Koch et al. | |
| 5,246,530 | A | 9/1993 | Bugle et al. | |
| 5,258,098 | A | 11/1993 | Wagner et al. | |
| 5,268,068 | A | 12/1993 | Cowell et al. | 156/644 |
| 5,271,736 | A | 12/1993 | Picha | |
| 5,298,115 | A | 3/1994 | Leonard | 156/645 |
| 5,307,594 | A | 5/1994 | Panchison | |
| 5,358,533 | A | 10/1994 | Noiles et al. | |
| 5,456,723 | A | 10/1995 | Steinemann et al. | 623/16 |
| 5,484,074 | A | 1/1996 | Deibler et al. | 216/12 |
| 5,507,815 | A | 4/1996 | Wagner et al. | 623/16 |
| 5,526,950 | A | 6/1996 | Tago et al. | 216/12 |
| 5,549,704 | A | 8/1996 | Sutter | |
| 5,571,017 | A | 11/1996 | Niznick | |
| 5,603,338 | A | 2/1997 | Beaty | 128/898 |
| 5,606,589 | A | 2/1997 | Pellegrino et al. | 378/154 |
| 5,607,480 | A | 3/1997 | Beaty | |
| 5,639,237 | A | 6/1997 | Fontenot | |
| 5,645,593 | A | 7/1997 | Woods et al. | |
| 5,658,334 | A | 8/1997 | Caldarise et al. | |
| 5,665,118 | A | 9/1997 | LaSalle et al. | |
| 5,665,121 | A | 9/1997 | Gie et al. | |
| 5,676,850 | A | 10/1997 | Reed et al. | |
| 5,709,804 | A | 1/1998 | Makita et al. | 216/12 |
| 5,713,410 | A | 2/1998 | LaSalle et al. | |
| 5,716,412 | A | 2/1998 | DeCarlo, Jr. et al. | |
| 5,728,159 | A | 3/1998 | Stroever et al. | |
| 5,730,887 | A | 3/1998 | Simpson et al. | 216/12 |
| 5,814,235 | A | 9/1998 | Pellegrino et al. | 216/12 |
| 5,826,586 | A | 10/1998 | Mishra et al. | |
| 5,830,373 | A | 11/1998 | Ohtake et al. | 216/12 |
| 5,843,250 | A | 12/1998 | Bone et al. | |
| 5,853,561 | A | 12/1998 | Banks | 205/646 |
| 5,897,592 | A | 4/1999 | Caldarise et al. | |
| 5,910,173 | A | 6/1999 | DeCarlo, Jr. et al. | |
| 5,922,029 | A | 7/1999 | Wagner et al. | 623/66 |
| 5,965,006 | A | 10/1999 | Baege et al. | 205/666 |
| 5,975,903 | A | 11/1999 | Shoher et al. | |
| 6,005,164 | A | 12/1999 | Johansson et al. | |
| 6,008,430 | A | 12/1999 | White | |
| 6,008,431 | A | 12/1999 | Caldarise et al. | |
| 6,008,432 | A | 12/1999 | Taylor | |
| 6,010,336 | A | 1/2000 | Shimotoso et al. | |
| 6,069,295 | A | 5/2000 | Leitao | |
| 6,095,817 | A | 8/2000 | Wagner et al. | |
| 6,106,558 | A | 8/2000 | Picha | |
| 6,149,688 | A | 11/2000 | Brosnahan et al. | |
| 6,149,689 | A | 11/2000 | Grundei | |
| 6,171,344 | B1 | 1/2001 | Atala | |
| 6,193,762 | B1 | 2/2001 | Wagner et al. | |
| 6,200,346 | B1 | 3/2001 | Baege et al. | |
| 6,217,333 | B1 | 4/2001 | Ercoli | |
| 6,217,615 | B1 | 4/2001 | Sioshansi et al. | |
| 6,221,109 | B1 | 4/2001 | Geistlich et al. | |
| 6,235,638 | B1 | 5/2001 | Huang et al. | |
| 6,261,322 | B1 | 7/2001 | Despres, III et al. | |
| 6,270,530 | B1 | 8/2001 | Eldridge et al. | |
| 6,277,150 | B1 | 8/2001 | Crawley et al. | |
| 6,312,612 | B1 | 11/2001 | Sherman et al. | |
| 6,315,798 | B1 | 11/2001 | Ashbly et al. | |
| 6,344,061 | B1 | 2/2002 | Leitao et al. | |
| 2001/0039454 | A1 | 11/2001 | Ricci et al. | |

METHOD FOR MAKING A MESH-AND-PLATE SURGICAL IMPLANT

CROSS-REFERENCE TO RELATED APPLICATIONS

This application claims priority to U.S. Provisional Application Ser. No. 60/309,923, filed Aug. 3, 2001, U.S. Provisional Patent Application Ser. No. 60/291,002, filed May 15, 2001, and U.S. Provisional Patent Application Ser. No. 60/264,084, filed Jan. 25, 2001.

BACKGROUND OF THE INVENTION

1. Field of the Invention

The invention relates to surgical implants, and is directed more particularly to the making of such implants having relatively rigid plate portions and pliable, textured, mesh portions, either portion being provided with at least one screw hole to facilitate attachment to bone.

2. Description of the Prior Art

The use of surgical implants is well known. Surgically implantable metal devices generally are formed of plates or sheets of inert metal, such as titanium, compatible with human and animal tissue. When such implants are positioned between bone and soft tissue, a textured, roughened traction surface in contact with the bone promotes ingrowth of the bone, bonding with the traction surface and enhancing the permanent, stable positioning of the implant. Textured bone-contacting surfaces thus enhance the stability of the metal implants after surgery. The desirablility of rough, textured, bone-engaging surfaces to assure stable positioning of surgical implants has been recognized and has been discussed in U.S. Pat. No. 5,258,098, issued Nov. 2, 1993, in the names of Donald J. Wagner et al, U.S. Pat. No. 5,298,115, issued Mar. 29, 1994, in the name of Ian Leonard, U.S. Pat. No. , 5,456,723, issued Oct. 10, 1995, in the names of Samuel G. Steinemann et al, U.S. Pat. No. 5,507,815, issued Apr. 16, 1996, in the names of Donald J. Wagner et al, U.S. Pat. No. 5,603,338, issued Feb. 18, 1997, in the name of Keith D. Beaty, U.S. Pat. No. , 5,853,561, issued Dec. 29, 1998, in the name of Bruce A. Banks, U.S. Pat. No. 5,922,029, issued Jul. 13, 1999, in the names of Donald J. Wagner et al, and U.S. Pat. No. 5,965,006, issued Oct. 12, 1999, in the names of Roland Baege et al.

Some implants are formed as thin mesh sheets, of extremely light weight and with numerous openings therethrough. In some cases, bendable mesh implants require relatively stiff, unbendable reinforcing plate portions. The formation of perforated thin metallic sheets, or plates, is described in several U.S. patents, including U.S. Pat. No. 3,359,192, issued Dec. 19, 1967, in the names of Hans-Joachim Heinrich et al, U.S. Pat. No. 5,606,589, issued Feb. 25, 1997, in the names of Anthony J. Pellegrino et al, and U.S. Pat. No. 5,814,235, issued Sep. 29, 1998, in the names of Anthony J. Pellegrino et al. Through-holes penetrating such plate portions are useful for receiving mounting screws, anchoring the mesh-and plate implant in position. However, the manufacture of such implants combining a relatively thin pliable sheet with a thicker unbendable plate, and with mounting screw holes therein, has presented some challenges still lacking feasible and economical solutions.

SUMMARY OF THE INVENTION

An object of the invention is, therefore, to provide a method for making a mesh-and-plate surgical implant including bendable perforated mesh portions adjoining stiff, rigid reinforcing plate portions.

A further object is to provide a method for making such implants having therein mounting screw holes which pass therethrough, for receiving mounting screws installed during implantation.

With the above and other objects in view, a feature of the present invention is the provision of a method for making a mesh-and-plate surgical implant, the method comprising the steps of applying maskant to first and second faces of a metal sheet, selectively ablating the maskant on both faces, affixing a first protective tape to the first face to cover same and maskant thereon, but leaving exposed a portion for a screw hole, affixing a second protective tape to the second face to cover same and maskant thereon, etching the first face screw hole portion to form a crater, removing the first tape, etching the crater and other exposed portions of the first face, removing the second tape, etching opposite the crater and other exposed portions of the second face to provide an opening in communication with the crater, and to provide other second face openings extending to the first face, and removing remaining maskant to provide the implant configured to include a pliable mesh portion and a rigid plate portion, and having screw holes therein.

The above and other features of the invention, including various novel details of construction and combinations of method steps, will now be more particularly described with reference to the accompanying drawings and pointed out in the claims. It will be understood that the particular method embodying the invention is shown and described by way of illustration only and not as a limitation of the invention. The principles and features of this invention may be employed in various and numerous embodiments without departing from the scope of the invention.

BRIEF DESCRIPTION OF THE DRAWINGS

Reference is made to the accompanying drawings in which is shown an illustrative embodiment of the invention, from which its novel features and advantages will be apparent.

In the drawings.

DESCRIPTION OF THE PREFERRED EMBODIMENT

Figure 1:
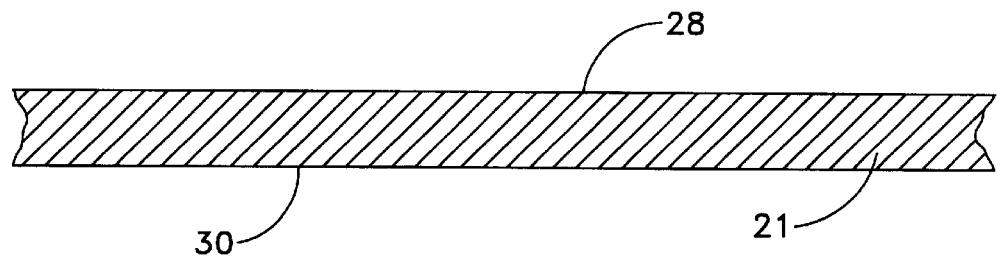
FIGS. 1–10 are diagrammatic cross-sectional views of successive stages in the making of a mesh-and-plate implant in accordance with an embodiment of the invention.

To make a mesh-and-plate surgical implant, there is provided a thin sheet 21 (FIG. 1) of tissue and bone compatible metal, such as titanium.

Figure 2:
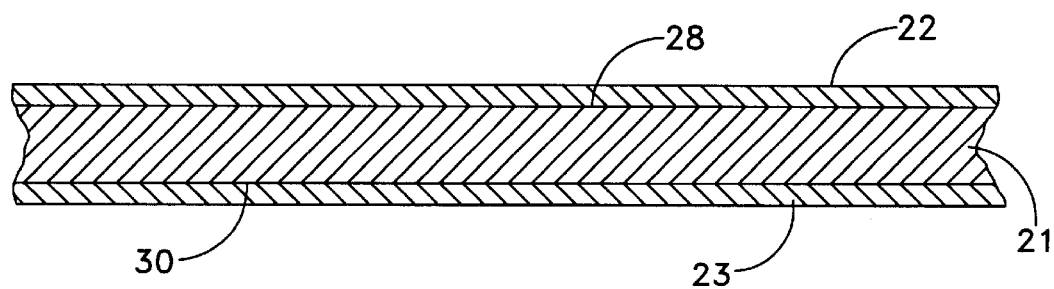

A maskant layer 22 (FIG. 2) is applied to a first face 28 of the sheet 21 and a maskant layer 23 is applied to a second face 30 of the sheet 21. The maskant layers 22,23 cover substantially the entirety of the first and second faces 28, 30, respectively. The maskant layers 22, 23 are resistant to chemical attack. It has been found that a photo-chemical resist, such as duPont Riston, or Kodak Thin Film Resist, serve as appropriate materials for the maskant layers 22, 23.

Figure 3:
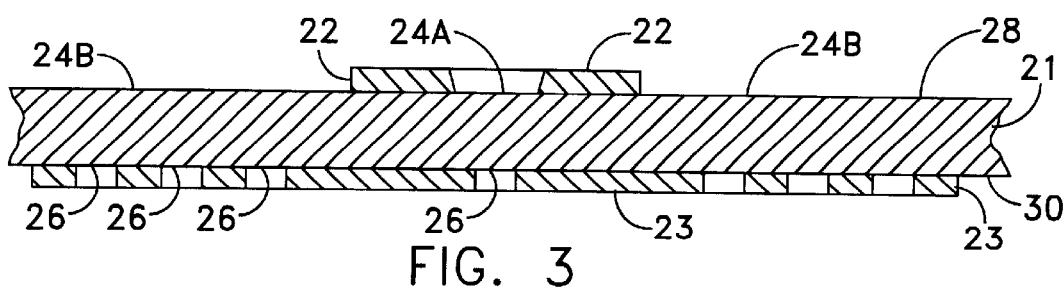

The maskant layers 22, 23 are then in part ablated from selected portions of the metal faces 28, 30 (FIG. 3), as by mechanical tools, chemical milling, photo-chemical etching, or by laser eradication, to expose portions 24A, 24B, 26 of the respective metal faces 28, 30 in desired patterns, ready for etching.

Figure 4:
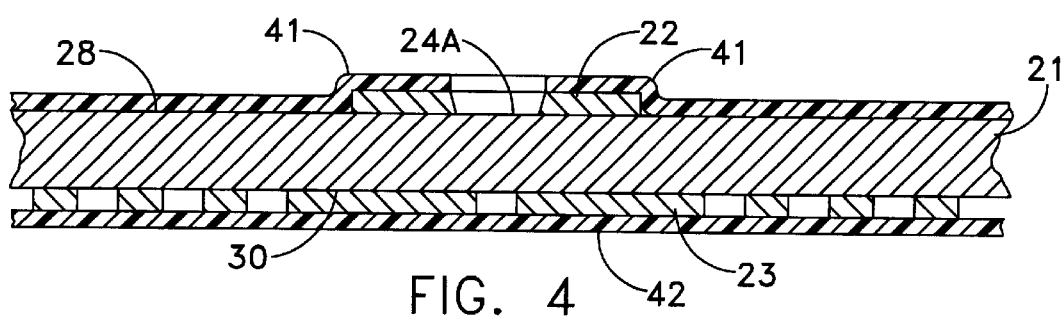

Referring to FIG. 4, it will be seen that the exposed portions 24B of the first face 28 and the maskant layer 22 on the first face 28 are covered with a protective tape 41, leaving exposed only the region 24A where a central through-hole is desired for acceptance of a mounting screw (not shown). Similarly, the exposed portions 26 of the second face 30 and the maskant layer 23 on the second face 30 are covered with a protective tape 42. The tapes 41, 42 may be 3M Brand Type #1280 Platers Tape.

The through-hole region 24A is then subjected to etching, as by spray or immersion, using an acid bath of a mixture of nitric and hydrofluoride acid. It is preferred, during the etching process, to periodically remove the sheet 21 from the etching process and rinse, dry and bake the sheet to maintain the integrity of the maskant and allow for in-process inspections.

Figure 5:
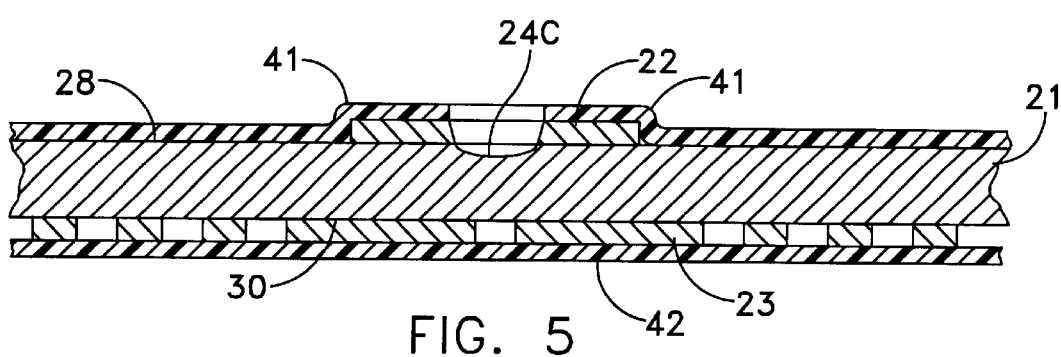
Figure 6:
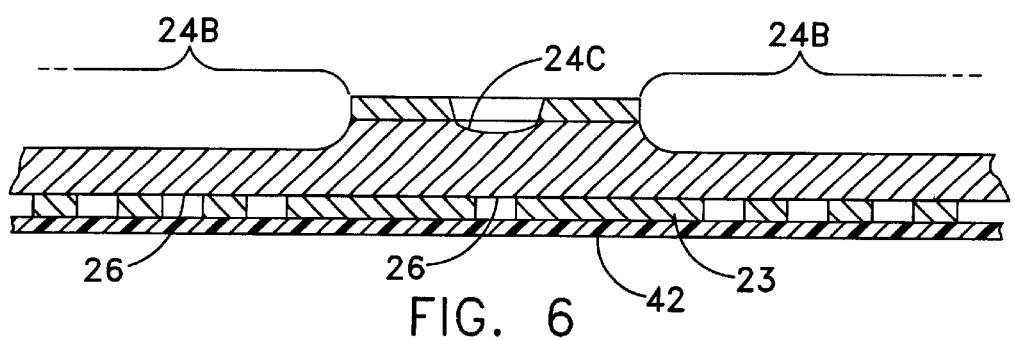
Figure 7:
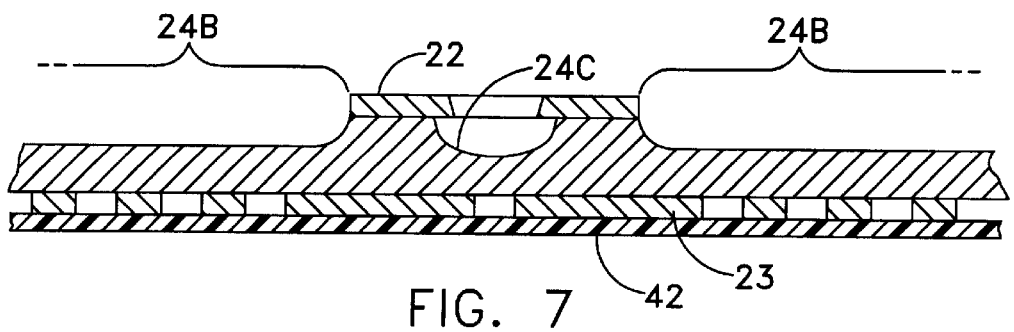
Figure 8:
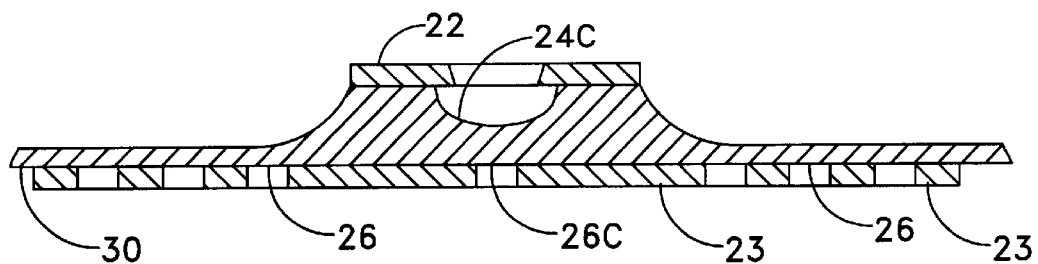

When the etchant reaching the exposed surface 24A has created a shallow crater 24C (FIG. 5), the protective tape 41 is removed (FIG. 6) and the etching of the crater 24C is resumed, and etching of the exposed portions 24B, constituting the mesh portion of the implant, is undertaken. As etching proceeds, the exposed metal regions 24C and 24B are progressively removed by the etchant (FIG. 7). The etching continues until the removal of metal from the first face 28 and crater 24C has reached the predetermined extent desired (FIG. 8).

The second tape 42 is then removed, exposing the maskant layer 23 and exposed portions 26 on the second face 30, including an area 26C opposite the crater 24C.

Figure 9:
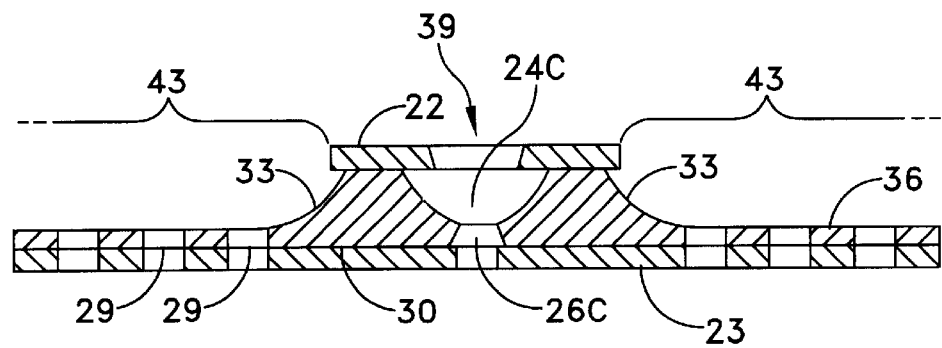

Etching of the through-hole area 26C in the sheet face 30 breaks through to the crater 24C to effect a counter-sunk through-hole 39 (FIG. 9) and second face openings 29 in communication with the newly etched first face 36.

Figure 10:
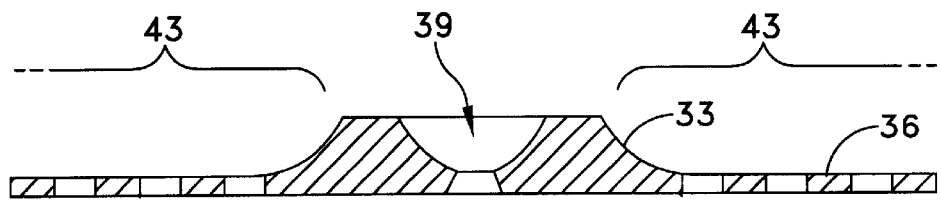

The first and second maskant layers 22, 23 are then removed (FIG. 10), leaving an implant device having the mesh portion 43, a plate portion 33, and at least one through-hole 39 for receiving a mounting screw.

Figure 11:
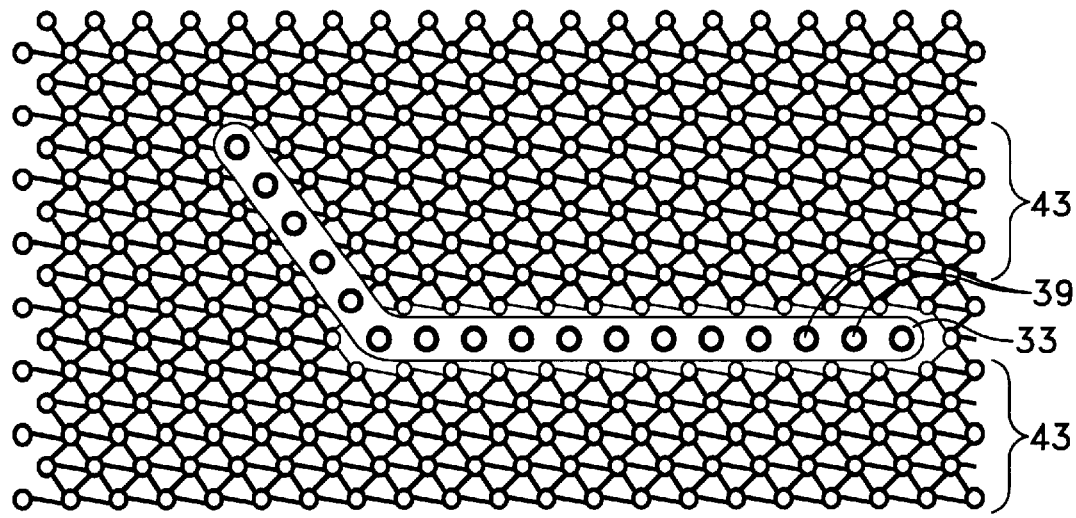
FIG. 11 is a top plan view of a mesh-and-plate implant made in accordance with the method illustrated in FIGS. 1–10.
Figure 12:
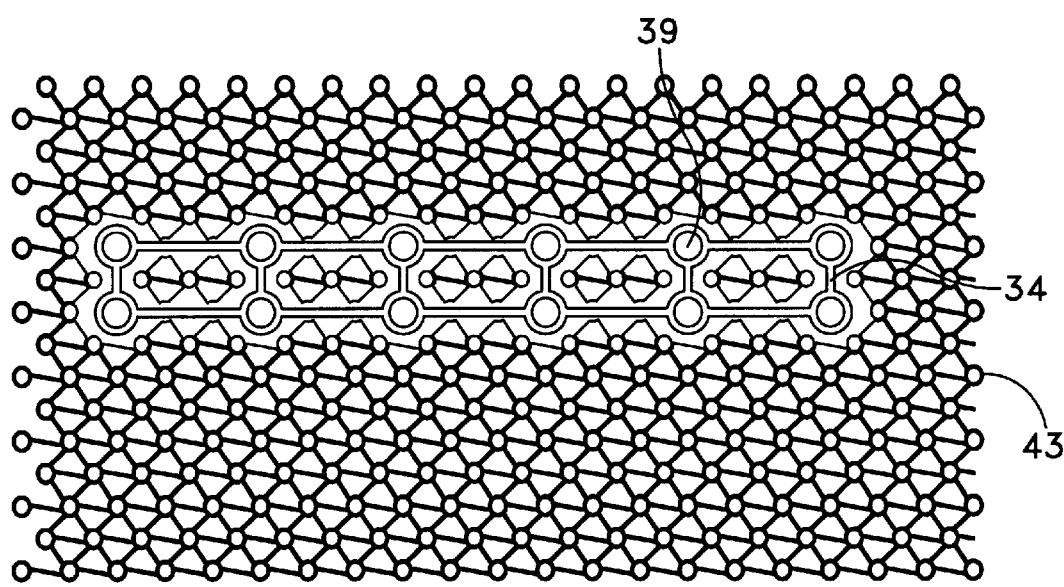
FIG. 12 is similar to FIG. 11, but illustrative of an alternative implant.

In FIG. 11 there is shown, for illustrative purposes, a dogleg plate portion 33 having one or more through-holes 39 therein, the plate portion 33 being bounded by the mesh portion 43. In FIG. 12 there is shown a divided plate 34 having through-holes 39 therein, and bounded by the mesh portion 43.

Figure 13:
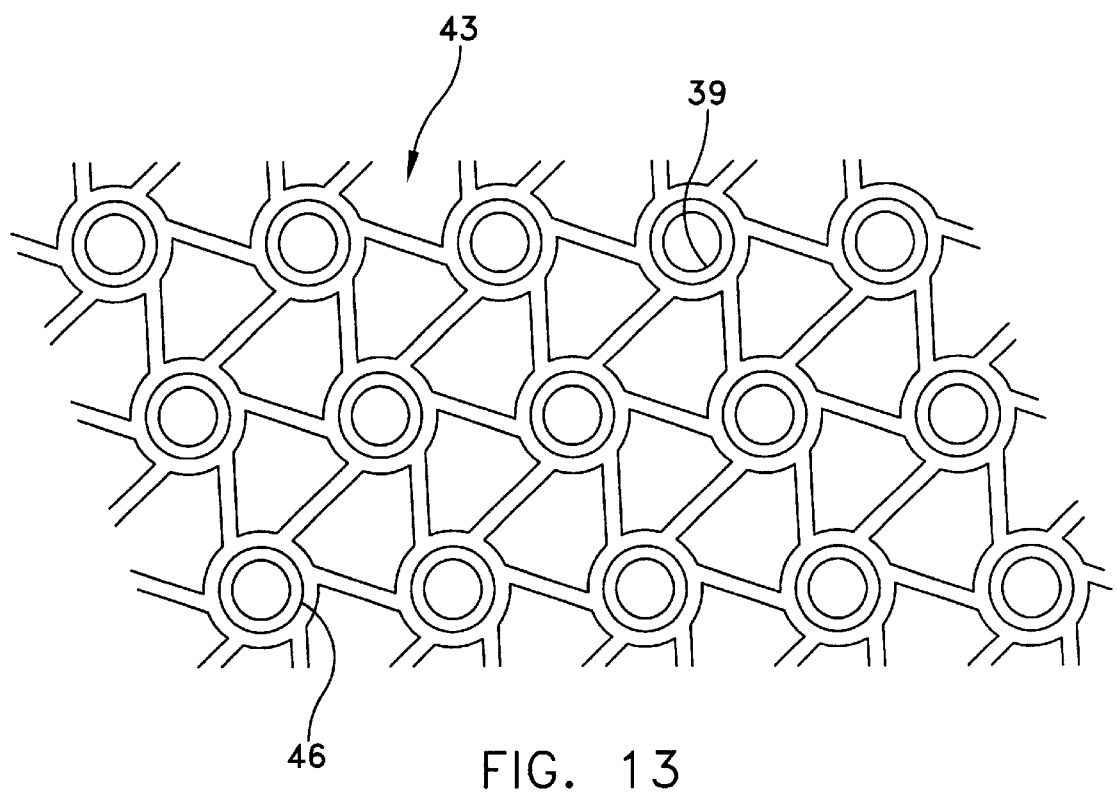
FIG. 13 is an enlarged illustration of the mesh portions of the implants of FIGS. 11 and 12.

Referring to FIG. 13, it will be seen that through-holes 39 may be provided in mesh portions 43, such through-holes preferably being surrounded by rim collars 46 comparable in thickness to a plate portion 33. The through-holes 39 preferably are countersunk to receive mounting screws.

In an alternative embodiment, the maskant layers 22, 23 may be exposed to a movable laser beam which is moved in accordance with a path governed by a CAD data file, wherein the beam removes unwanted maskant. After the laser removes the maskant, the sheet 21 is exposed to heat and/or ultraviolet light to cure and harden the remaining maskant.

The mesh portions 43 preferably are of a thickness of about 0.5 mm and are readily flexed to follow the curvature of a bone.

There is thus provided an improved method for making a mesh-and-plate surgical implant including both bendable perforated mesh portions and relatively rigid plate portions, wherein the bendable or comformable perforated portions are integral with and kinematically related to the rigid plate portions. The improved method further provides through-holes for receiving mounting screws during implantation.

It will be understood that many additional changes in the details, materials, steps and arrangement of parts, which have been herein described and illustrated in order to explain the nature of the invention, may be made by those skilled in the art within the principles and scope of the invention as expressed in the appended claims.

What is claimed is:

1. A method for making a mesh-and-plate surgical implant, the method comprising the steps of:

applying maskant to first and second faces of a metal sheet;

selectively ablating the maskant on both faces;

affixing a first protective tape to the first face to cover the first face and maskant thereon, but leaving an exposed portion of the first face for a screw hole;

affixing a second protective tape to the second face to cover the second face and maskant thereon;

etching the first face screw hole portion to form a crater;

removing the first tape;

etching the crater and other exposed portions of the first face;

removing the second tape;

etching opposite the crater and other exposed portions of the second face to provide an opening in communication with the crater, and to provide other second face openings extending to the first face; and removing remaining maskant to provide the implant configured to include a pliable mesh portion and a rigid plate portion having a screw hole therein.

2. The method in accordance with claim 1 wherein the application of maskant to a metal sheet comprises:

providing a metal sheet of substantially uniform thickness throughout; and applying the maskant as coatings on the first and second faces covering substantially all of the first and second faces.

3. The method in accordance with claim 2 wherein selectively ablating the maskant comprises ablating the maskant on the first and second faces in selected loci to expose underlying portions of the metal sheet first and second faces, to leave maskant in patterns defining configurations of desired plate and mesh portions, and to further expose an underlying portion of the metal sheet first and second faces defining a disposition of a desired screw hole in the desired plate portion.

4. The method in accordance with claim 3 wherein affixing the first protective tape comprises affixing the first tape so as to cover the exposed underlying portions of the first face and the maskant remaining on the first face, but leaving exposed the underlying portion defining the location of the desired screw hole.

5. The method in accordance with claim 4 wherein the step of etching the first face screw hole portion comprises etching away the portion of the underlying first face defining the location of the desired screw hole to form a crater in the first face.

6. The method in accordance with claim 5 wherein etching the crater and other exposed portions of the first face comprises removing metal from the crater to deepen the crater in the metal sheet, and removing metal from the other exposed portions of the first face to reduce the thickness of the metal sheet in the mesh portion thereof.

7. Method for making a mesh-and-plate surgical implant, the method comprising the steps of:

providing a metal sheet;

applying to first and second faces of the sheet coatings of maskant resistant to chemical attack;

ablating the maskant on the first and second faces in selected loci to expose underlying portions of the metal sheet first and second faces in selected patterns, to leave the maskant in patterns defining configurations of desired plate and mesh portions, and to further expose underlying portions of the metal sheet first and second faces defining a location of a of desired screw hole;

affixing a first protective tape to the first face so as to cover the exposed underlying portions of the first face and the maskant remaining on the first face, but leaving exposed the underlying portion defining the location of the desired screw hole;

affixing a second protective tape to the second face so as to cover the exposed underlying portions of the second face and the maskant remaining on the second face;

etching away the portion of the underlying first face defining the location of the desired screw hole, to form a crater in the first face;

removing the first protective tape;

etching the crater and other exposed portions of the first face to remove metal therefrom;

removing the second protective tape;

etching the second face opposite the crater and etching other exposed portions of the second face to provide an opening in communication with the crater and to provide other second face openings in communication with the first face; and removing remaining maskant to provide the implant with exposed first and second faces and configured in part as a pliable mesh portion, and in part as at least one rigid plate portion, and having at least one screw hole therein.

8. The method in accordance with claim 7 wherein the metal sheet provided is of substantially uniform thickness throughout, and the plate portion of the implant is substantially thicker than the mesh portion of the implant.

9. The method in accordance with claim 7 wherein the coatings of maskant applied to the first and second faces are applied to cover substantially all of the first and second faces of the sheet.

10. The method in accordance with claim 7 wherein etching the other exposed portions of the first face reduces the thickness of the sheet in areas of the sheet mesh portion.

* * * * *